United States Patent [19]

Wiggin et al.

[11] Patent Number: 4,657,409
[45] Date of Patent: Apr. 14, 1987

[54] METHOD FOR FREEZING-POINT DETERMINATION

[75] Inventors: Blanton C. Wiggin, Wellesley; Julian W. Philbrick, Natick, both of Mass.

[73] Assignee: Advanced Instruments, Inc., Needham, Mass.

[21] Appl. No.: 617,729

[22] Filed: Jun. 6, 1984

[51] Int. Cl.⁴ .................................................. G01N 25/04
[52] U.S. Cl. ........................................ 374/25; 374/16
[58] Field of Search .................... 374/16, 25, 27; 422/100; 436/2

[56] References Cited

U.S. PATENT DOCUMENTS

| | | | |
|---|---|---|---|
| 3,150,515 | 9/1964 | Malina | 374/16 |
| 3,203,226 | 8/1965 | Fiske, Jr. | 374/16 |
| 3,263,487 | 8/1966 | Fiske, Jr. | 374/16 |
| 3,667,280 | 6/1972 | Simpson | 374/25 |
| 4,248,830 | 2/1981 | Kallies et al. | 422/100 |
| 4,299,795 | 11/1981 | Bates | 422/100 |
| 4,304,119 | 12/1981 | Uchigaki | 374/25 |
| 4,484,822 | 12/1984 | Hancock | 374/16 |

FOREIGN PATENT DOCUMENTS

| | | | |
|---|---|---|---|
| 1296726 | 5/1962 | France | 374/16 |
| 1197565 | 7/1970 | United Kingdom | 374/16 |

OTHER PUBLICATIONS

Prager et al. "Freeze-Point Depression: New Method for Measuring Ultramicro Quantities of Fluid," in Science, 10/63, vol. 142, No. 3589, pp. 237–239.
Abele, "The Physical Background to Freeze Point Osmometry–its Medical Biological Applications", American Journal of Medical Electronics, Jan.–Mar. 1963, vol. 2, No. 1, pp. 32–41.

Primary Examiner—Charles Frankfort
Assistant Examiner—Thomas B. Will
Attorney, Agent, or Firm—Richard J. Birch

[57] ABSTRACT

A method for measuring the freezing point of a liquid utilizing non-adiabatic thermodynamics for the chilling chamber. The temperature of the chilling chamber in which the measurement is made is actively altered to reduce net heat flow from the sample portion of the liquid being measured at least during nucleation of the sample portion. By actively altering the chilling-chamber temperature, the thermodynamics of the sample itself more nearly approach a true adiabatic condition during nucleation. Preferably, the freezing-point measurement is made in the sample-handling or pick-up device itself.

15 Claims, 4 Drawing Figures

METHOD FOR FREEZING-POINT DETERMINATION

BACKGROUND OF THE INVENTION

From the inception of freezing-point determination by Raoult, van't Hoff, Beckmann, et al., all freezing-point work has been done at constant temperature. The heat sink or heat source has been carefully controlled with improvements being made in thermostats and insulation to achieve an adiabatic condition during the freezing-point process. These methods have a limit on their inherent precision and repeatability because of overshooting, supercooling and other temperature reversals in the measurement cycle. Because of this, they are not adequate for working with very small samples, or for determining high molecular weights or precise chemical purity. As a result, other techniques are currently employed for such determinations.

It is accordingly, a general object of the present invention to provide an improved method for measuring the freezing-point of a liquid.

It is a specific object of the invention to provide a method for measuring the freezing point of a liquid in which non-adiabatic thermodynamics are employed in the chilling chamber to produce a more nearly true adiabatic condition in the liquid sample during nucleation.

It is another object of the invention to provide a method for measuring the freezing point of a liquid in which the net heat flow from the sample portion of the liquid under measurement is reduced at least during nucleation of the sample portion of the liquid.

It is a feature of the invention that the method can be used with very small samples and for determining higher molecular weights or precise chemical purity.

It is another feature of the invention that the method provides increased precision and repeatability over the prior art adiabatic freezing- and melting-point techniques.

BRIEF SUMMARY OF THE INVENTION

The present invention utilizes non-adiabatic thermodynamics in which the net heat flow from the sample portion of the liquid being measured is actively adjusted to be reduced at least during nucleation of the sample. In the preferred embodiment, the net heat-flow reduction is accomplished during nucleation by actively increasing the temperature of the bath or heat-transfer medium.

Preferably, instead of transferring the sample to a separate, intermediate container, such as a test tube, for placing in the freezing-point apparatus, the freezing- or melting-point determination is made right in the transfer medium, typically a pipette or a cylinder without ends for a flow-through sample process. In the latter case, the sample under test is not discharged into a test chamber, rather, the sample pick-up chamber itself becomes the test chamber. However, it should be understood that the thermodynamic technique of the invention is applicable to both an intermediate (test tube) and a direct sample-handling device.

BRIEF DESCRIPTION OF THE DRAWINGS

The objects and features described above and other objects and features of the invention will best be understood from a detailed description of the method of the invention as described in connection with the following drawings.

DETAILED DESCRIPTION OF THE METHOD OF THE INVENTION

Turning now to the drawings, the novel method for measuring the freezing point of a liquid will be described in connection with a representative example of an apparatus (FIGS. 1-3) capable of performing the method, and then the thermodynamics of the method will be described in connection with the sample and bath Time-Temperature plots of FIG. 4.

Figure 1:
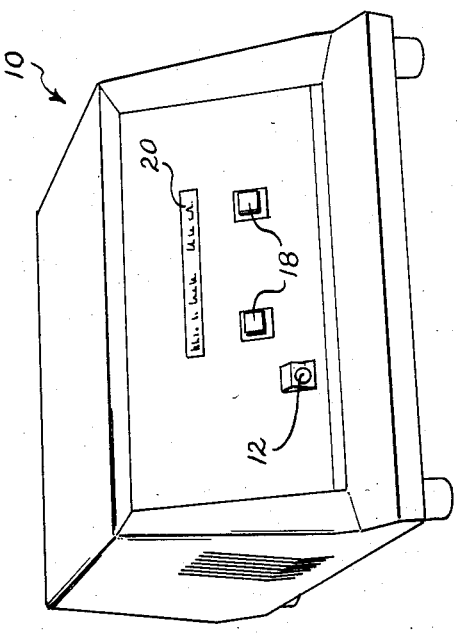
FIG. 1 is a view in perspective of a representative freezing-point apparatus capable of performing the method of the present invention.

FIG. 1 illustrates in perspective a representative apparatus indicated generally by the reference numeral 10 for performing a freezing-point determination or measurement of a sample portion of a liquid. Conventional cryoscopes and osmometers can be modified to achieve the desired non-adiabatic thermodynamics of the chilling chamber during freezing-point determination as will be described below. For the moment, it is sufficient to observe that the freezing-point apparatus 10 has a sample port 12 for receiving a sample container, indicated generally by the reference numeral 14 in FIG. 2. The sample container 14 is inserted into a chilling chamber, indicated generally by the reference numeral 16 in FIG. 2 which controls the temperature of the sample during the freezing-point determination process. The freezing-point apparatus 10 has conventional controls 18 and information displays 20.

Figure 3:
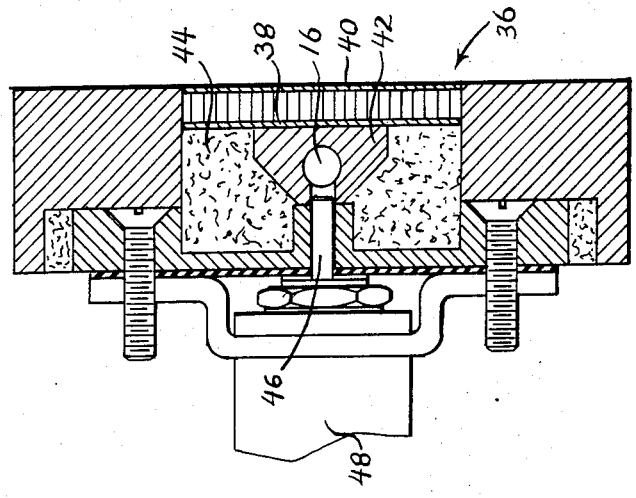
FIG. 3 is a view in partial section taken along lines 3—3 of FIG. 2.
Figure 2:
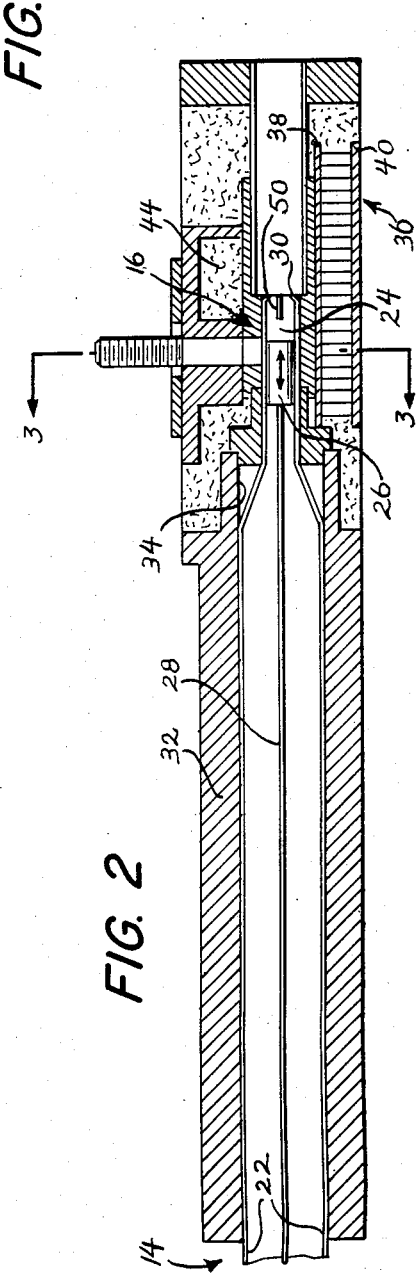
FIG. 2 is a view in partial section showing a liquid-sample-containing syringe positioned within the chilling-nucleation station of the freezing-point apparatus of FIG. 1.

Referring now to FIGS. 2 and 3, the sample container 14 can take a variety of conventional forms, such as a pipette or syringe. Preferably, the freezing-point measurement is performed while the liquid sample is in the sample-handling or pick-up device itself or at the sample-measuring station in the case of a flow-through configuration. This arrangment avoids the necessity of using an intermediate sample-handling device, e.g., a test tube. However, as previously mentioned, the thermodynamic technique can be employed with intermediate sample-handling devices.

The sample-handling device 14 shown in FIG. 2 is merely illustrative of a variety of sample-handling or pick-up devices. Thus, for purposes of illustration, the device 14 is shown as a syringe having cylindrical walls 22 that taper inwardly to form a sample containing chamber 24. The size of the sample chamber 24 is controlled by the position of a movable piston 26 actuated by means of a hand-operated piston rod 28. The sample to be measured is picked up by means of suction created by movement of the piston 26 away from the distal end 30 of the sample-containing device 14.

As mentioned previously, the sample-containing device 14 is inserted into the freezing-point apparatus sample port 12. The sample port 12 is formed by a cylindrical wall 32 (FIG. 2) which defines a sample container receiving bore 34. The sample port bore terminates in chilling chamber or station 16.

The chilling chamber or station 16 comprises a Peltier thermo-electric chiller indicated generally by the reference numeral 36. The Peltier chiller has first and second surfaces 38 and 40, respectively, that become "hot" or "cold" surfaces depending upon the direction of current flow through the thermo-electric device. A bored metal block 42 is positioned in thermally conductive contact with the Peltier thermo-electric chiller first surface 38. Thermal insulation 44 surrounds the bored metal block 42 to thermally isolate the block from its environment other than the first surface 38 of the Peltier thermo-electric chiller. It will be apparent that other types of a chiller-warmer, such as Freon compressor and electric resistor, will serve.

The metal block bore 32 is designed to receive the sample chamber portion 24 of the sample-containing device as shown in FIG. 2. With the sample-containing chamber portion 24 positioned within the bore of metal block 42, the Peltier thermo-electric device is actuated so that the first surface 38 is in thermal contact with the metal block (and therefore in thermal contact with the liquid sample in sample chamber 24) becomes the "cold" side of the thermo-electric chiller and the second surface 40 becomes the "hot" side. In one embodiment, nucleation of the liquid sample is initiated by the conventional technique of mechanical shock provided by a plunger 46 which is driven by a solenoid 48.

Figure 4:
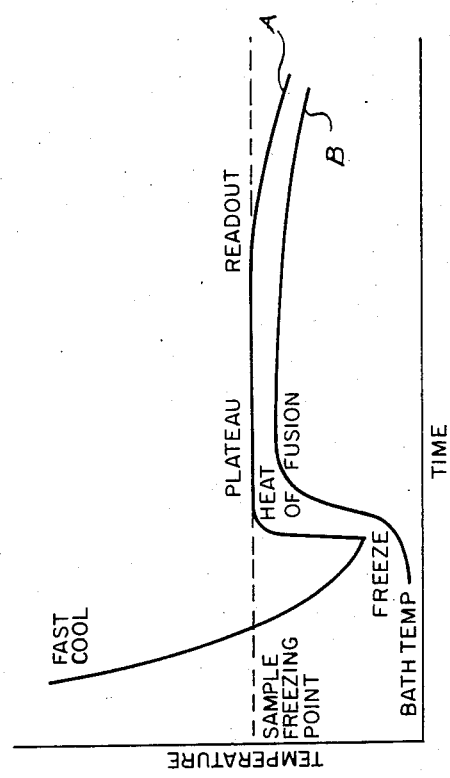
FIG. 4 is a Time-Temperature plot of sample and bath temperature showing the thermodynamics of the method of the present invention.

Referring now to FIG. 4, there are shown plots of the thermodynamics of sample freezing-point measurement. The sample temperature curve "A" is plotted with respect to temperature (ordinate) and time (abscissa). Starting at the top of the sample curve, as shown in FIG. 4, after the sample has been presented to the thermister probe 50 (FIG. 2), the sample is rapidly cooled by means of the Peltier thermo-electric chiller 36. As the temperature of the sample reaches approximately 0° C., the cooling rate of the sample slows. After the sample has been sufficiently supercooled, a mechanical pulse produced by solenoid actuated plunger 46 induces the sample to freeze. At this point, the heat of fusion from the sample and raises the temperature to the actual freezing point of the sample. Thereafter, the sample temperature remains relatively level as indicated by the plateau portion of the curve. In conventional freezing-point determination machines, the "bath" temperature "B" is held constant (i.e., adiabatic) from supercooling or nucleation as described above in connection with curve "A".

The terms "bath" "chiller" and "heat-transfer medium" are used herein broadly an synonymously, whether fluids or solids. In the case of the representative apparatus shown in FIGS. 1-3, the heat-transfer medium constitutes the metal block 42 which is in thermally conductive contact with the Peltier thermo-electric chiller 36.

It has already been mentioned that one of the objects of the present invention is to provide a method for measuring the freezing point of a liquid utilizing non-adiabatic thermodynamics for the chiller. The method of the present invention is accomplished by actively altering the temperature of the chiller to reduce net heat flow from the sample portion of the liquid at least during nucleation. The reduction of the heat flow is achieved in the representative apparatus 10 by reversing the Peltier thermo-electric chiller 36 so that the first surface 38 is the hot side of the device while the second surface 40 is the cold side of the device. The reversal of the hot and cold sides of the thermo-electric device 36 produces a non-constant bath temperature as shown by curve "B" in FIG. 4. Curve "B" depicts the temperature of the bath, in this case the temperature of the metal block 42.

The reduction of net heat flow is performed at least during nucleation and f-p measurement of the sample portion. As shown in FIG. 4, the net heat flow reduction can be initiated prior to the induction of nucleation in order to overcome the thermal inertia of the bath. Again, in the representative freezing-point apparatus of FIGS. 1-3, reduction in net heat flow prior to nucleation is achieved by reversing the hot and cold polarities of the Peltier device 36.

It will be appreciated that conventional freezing point apparatus, e.g. cryoscopes and osmometers, can be modified to perform the method of the present invention. In each case, the apparatus is modified to operate in a non-adiabatic mode to permit alteration of bath temperature to reduce net heat flow from the sample at least during nucleation. Given the present use of the reversible thermo-electric chillers, such chillers can be incorporated in existing freezing-point apparatus. For those units that already employ thermal-electric chillers, the method can be implemented by reversing the hot and cold sides as described above to achieve bath temperatures as shown in plot "B" of FIG. 4.

Having described in detail the method of our invention, it will now be appreciated to those skilled in the art that numerous modifications can be made therein without departing from the scope of the invention as defined in the following claims:

What we claim and desire to secure by Letters Patent of the United States is:

1. A method for measuring the freezing point of a liquid comprising the steps of:
   picking up sample portion of the liquid to be measured in a thermally conductive sample-pickup device;
   reducing the temperature of the sample portion of the liquid to a temperature below the normal freezing point temperature of the liquid while the sample portion is in the sample-pickup device;
   inducing nucleation of the sample portion of the liquid in the sample-pickup device;
   reducing net heat flow from the sample portion of the liquid at least during nucleation of the sample portion of the liquid in order to extend the duration of the plateau portion of the thermodynamic curve and to produce a slope at the end of the plateau portion having an opposite sign to the slope of the approach to the plateau portion; and,
   thereafter measuring the temperature of the nucleated sample portion of the liquid in the sample-pickup device at the plateau maximum.

2. A method for measuring the freezing point of a liquid comprising the steps of:
   placing a sample portion of the liquid to be measured in a thermally conductive sample-handling device;
   reducing the temperature of the sample portion of the liquid to a temperature below the normal freezing point temperature of the liquid by placing the sample-handling device in thermally conductive contact with a heat sink;
   inducing nucleation in the sample portion of the liquid in the sample-handling device;

reducing net heat flow from the sample portion of the liquid at least during nucleation of the sample portion of the liquid in order to extend the duration of the plateau portion of the thermodynamic curve and to produce a slope at the end of the plateau portion having an opposite sign to the slope of the approach to the plateau portion; and, thereafter measuring the temperature of the nucleated sample portion of the liquid in the sample-handling device at the plateau maximum.

3. A method for measuring the freezing point of a liquid comprising the steps of:

placing a sample portion of the liquid to be measured in a thermally conductive sample-handling device;

reducing the temperature of the sample portion of the liquid to a temperature below the normal freezing point temperature of the liquid by placing the sample-handling device in thermally conductive contact with a heat sink;

inducing nucleation in the sample portion of the liquid in the sample-handling device;

reducing net heat flow from the sample portion of the liquid prior to and during nucleation of the sample portion of the liquid in order to extend the duration of the plateau portion of the thermodynamic curve and to produce a slope at the end of the plateau portion having an opposite sign to the slope of the approach to the plateau portion; and, thereafter measuring the temperature of the nucleated sample portion of the liquid in the sample-handling device at the plateau maximum.

4. A method for measuring the freezing point of a liquid comprising the steps of:

placing a sample portion of the liquid to be measured in a thermally conductive sample-handling device;

reducing the temperature of the sample portion of the liquid to a temperature below the normal freezing point temperature of the liquid by placing the sample-handling device in thermally conductive contact with a heat sink;

inducing nucleation in the sample portion of the liquid in the sample-handling device;

reducing net heat flow from the sample portion of the liquid at least during nucleation of the sample portion of the liquid by actively increasing the temperature of the heat sink in order to extend the duration of the plateau portion of the thermodynamic curve and to produce a slope at the end of the plateau portion having an opposite sign to the slope of the approach to the plateau portion; and, thereafter measuring the temperature of the nucleated sample portion of the liquid in the sample-handling device at the plateau maximum.

5. A method for measuring the freezing point of a liquid comprising the steps of:

placing a sample portion of the liquid to be measured in a thermally conductive sample-handling device;

placing the sample containing sample-handling device in thermally conductive contact with a heat-transfer medium;

reducing the temperature of the sample portion of the liquid to a temperature below the normal freezing point temperature of the liquid by reducing the temperature of the heat-transfer medium;

inducing nucleation of the sample portion of the liquid in the sample-handling device;

reducing net heat flow from the sample portion of the liquid at least during nucleation of the sample portion of the liquid by actively increasing the temperature of the heat-transfer medium in order to extend the duration of the plateau portion of the thermodynamic curve and to produce a slope at the end of the plateau portion having an opposite sign to the slope of the approach to the plateau portion; and, thereafter measuring the temperature of the nucleated sample portion of liquid in the sample-handling device at the plateau maximum.

6. A method for measuring the freezing point of a liquid comprising the steps of:

placing a sample portion of the liquid to be measured in a thermally conductive sample-handling device;

placing the sample containing sample-handling device in thermally conductive contact with a heat-transfer medium;

reducing the temperature of the sample portion of the liquid to a temperature below the normal freezing point temperature of the liquid by reducing the temperature of the heat-transfer medium;

inducing nucleation of the sample portion of the liquid in the sample-handling device;

reducing net heat flow from the sample portion of the liquid prior to and during nucleation of the sample portion of the liquid by increasing the temperature of the heat-transfer medium in order to extend the duration of the plateau portion of the thermodynamic curve and to produce a slope at the end of the plateau portion having an opposite sign to the slope of the approach to the plateau portion; and, thereafter measuring the temperature of the nucleated sample portion of liquid in the sample-handling device at the plateau maximum.

7. The method of claim 5 or 6 wherein the net heat flow is reduced so that temperature of the heat-transfer medium tracks the temperature of the sample portion of the liquid during nucleation whereby the temperature difference between the nucleating liquid and the heat-transfer medium is minimized.

8. A method for measuring the freezing point of a liquid comprising the steps of:

placing a sample portion of the liquid to be measured in a sample-measuring station;

reducing the temperature of the sample portion of the liquid to a temperature below the normal freezing point temperature of the liquid by placing the sample portion of the liquid to be measured in direct thermally conductive contact with a heat sink;

inducing nucleation in the sample portion of the liquid in the sample-measuring station;

altering net heat flow with respect to the sample portion of the liquid at least during nucleation of the sample portion of the liquid by increasing the temperature of the heat sink in order to extend the duration of the plateau portion of the thermodynamic curve and to produce a slope at the end of the plateau portion having an opposite sign to the slope of the approach to the plateau portion; and, thereafter measuring the temperature of the nucleated sample portion of liquid in the sample-measuring station at the plateau maximum.

9. A method for measuring the freezing point of a liquid comprising the steps of:

placing a sample portion of the liquid to be measured in a sample-measuring station;

placing the sample portion of the liquid to be measured in thermally conductive contact with a heat-transfer medium;

reducing the temperature of the sample portion of the liquid to a temperature below the normal freezing point temperature of the liquid by reducing the temperature of the heat-transfer medium;

inducing nucleation of the sample portion of the liquid in the sample-measuring station;

altering net heat flow with respect to the sample portion of the liquid at least during nucleation of the sample portion of the liquid by increasing the temperature of the heat-transfer medium in order to extend the duration of the plateau portion of the thermodynamic curve and to produce a slope at the end of the plateau portion having an opposite sign to the slope of the approach to the plateau portion; and, thereafter measuring the temperature of the nucleated sample portion of liquid in the sample-measuring station at the plateau maximum.

10. A method for measuring the freezing point of a liquid comprising the steps of:

placing a sample portion of the liquid to be measured in a sample-measuring station;

placing the sample portion of the liquid to be measured in thermally conductive contact with a heat-transfer medium;

reducing the temperature of the sample portion of the liquid to a temperature below the normal freezing point temperature of the liquid by reducing the temperature of the heat-transfer medium;

inducing nucleation of the sample portion of the liquid in the sample-measuring station;

altering net heat flow with respect to the sample portion of the liquid prior to and during nucleation of the sample portion of the liquid by increasing the temperature of the heat-transfer medium in order to extend the duration of the plateau portion of the thermodynamic curve and to produce a slope at the end of the plateau portion having an opposite sign to the slope of the approach to the plateau portion; and, thereafter measuring the temperature of the nucleated sample portion of liquid in the sample-measuring station at the plateau maximum.

11. A method for measuring the freezing point of a liquid comprising the steps of:

obtaining a sample portion of the liquid to be measured;

reducing the temperature of the sample portion of the liquid to a temperature below the normal freezing point temperature of the liquid;

inducing nucleation of the sample portion of the liquid;

actively reducing net heat flow from the sample portion of the liquid at least during nucleation of the sample portion of the liquid in order to extend the duration of the plateau portion of the thermodynamic curve and to produce a slope at the end of the plateau portion having an opposite sign to the slope of the approach to the plateau portion; and, thereafter measuring the temperature of the nucleated sample portion of the liquid at the plateau maximum.

12. A method for measuring the freezing point of a liquid comprising the steps of:

obtaining a sample portion of the liquid to be measured;

reducing the temperature of the sample portion of the liquid to a temperature below the normal freezing point temperature of the liquid;

inducing nucleation in the sample portion of the liquid;

actively reducing net heat flow from the sample portion of the liquid prior to and during nucleation of the sample portion of the liquid in order to extend the duration of the plateau portion of the thermodynamic curve and to produce a slope at the end of the plateau portion having an opposite sign to the slope of the approach to the plateau portion; and thereafter measuring the temperature of the nucleated sample portion of liquid at the plateau maximum.

13. A method for measuring the freezing point of a liquid comprising the steps of:

obtaining a sample portion of the liquid to be measured;

reducing the temperature of the sample portion of the liquid to a temperature below the normal freezing point temperature of the liquid by placing the sample-handling device in thermally conductive contact with a heat sink;

inducing nucleation in the sample portion of the liquid;

altering net heat flow with respect to the sample portion of the liquid by actively raising the temperature of the heat sink at least during nucleation of the sample portion of the liquid in order to extend the duration of the plateau portion of the thermodynamic curve and to produce a slope at the end of the plateau portion having an opposite sign to the slope of the approach to the plateau portion; and, thereafter measuring the temperature of the nucleated sample portion of liquid at the plateau maximum.

14. A method for measuring the freezing point of a liquid comprising the steps of:

obtaining a sample portion of the liquid to be measured;

reducing the temperature of the sample portion of the liquid to a temperature below the normal freezing point temperature of the liquid by placing the sample-handling device in thermally conductive contact with a heat sink;

inducing nucleation of the sample portion of the liquid;

altering net heat flow with respect to the sample portion of the liquid by actively raising the temperature of the heat sink prior to and during nucleation of the sample portion of the liquid in order to extend the duration of the plateau portion of the thermodynamic curve and to produce a slope at the end of the plateau portion having an opposite sign to the slope of the approach to the plateau portion; and, thereafter measuring the temperature of the nucleated sample portion of liquid at the plateau maximum.

15. A method for measuring the freezing point of a liquid comprising the steps of:

obtaining a sample portion of the liquid to be measured;

reducing the temperature of the sample portion of the liquid to a temperature below the normal freezing point temperature of the liquid by placing the sample-handling device in thermally conductive contact with a heat sink;

inducing nucleation of the sample portion of the liquid;

altering net heat flow with respect to the sample portion of the liquid by actively raising the temperature of the heat sink prior to and during nucleation of the sample portion of the liquid to a temperature above that of the sample portion of the liquid at the commencement of nucleation in order to extend the duration of the plateau portion of the thermodynamic curve and to produce a slope at the end of the plateau portion having an opposite sign to the slope of the approach to the plateau portion; and, thereafter measuring the temperature of the nucleated sample portion of liquid at the plateau maximum.

* * * * *